(12) United States Patent
Jin

(10) Patent No.: US 9,526,676 B2
(45) Date of Patent: Dec. 27, 2016

(54) POLYMERIZABLE RESINS CONTAINING A 1,3,5-HEXAHYDRO-1,3,5-TRIAZINE MOIETY, METHODS OF MAKING, AND DENTAL COMPOSITIONS CONTAINING THE SAME

(71) Applicant: DENTSPLY International Inc., York, PA (US)

(72) Inventor: Xiaoming Jin, Middletown, DE (US)

(73) Assignee: Dentsply Sirona Inc., York, PA (US)

( * ) Notice: Subject to any disclaimer, the term of this patent is extended or adjusted under 35 U.S.C. 154(b) by 68 days.

(21) Appl. No.: 14/527,828

(22) Filed: Oct. 30, 2014

(65) Prior Publication Data

US 2015/0119488 A1    Apr. 30, 2015

Related U.S. Application Data

(60) Provisional application No. 61/897,247, filed on Oct. 30, 2013.

(51) Int. Cl.
*A61K 6/083* (2006.01)
*C07D 211/06* (2006.01)

(52) U.S. Cl.
CPC .............. *A61K 6/083* (2013.01); *C07D 211/06* (2013.01)

(58) Field of Classification Search
CPC ..................................................... A61K 6/083
See application file for complete search history.

(56) References Cited

U.S. PATENT DOCUMENTS

| 2,615,887 | A | | 6/1948 | Zerner et al. |
| 2,615,882 | A | * | 10/1952 | Zerner .................... C08F 20/60 |
| | | | | 526/261 |
| 2,651,631 | A | | 9/1953 | Zerner et al. |
| 2,794,737 | A | | 6/1957 | Lundberg et al. |
| 6,172,131 | B1 | | 1/2001 | Moszner et al. |
| 6,350,839 | B2 | | 2/2002 | Moszner et al. |
| 2010/0076157 | A1 | | 3/2010 | Sekiguchi et al. |
| 2014/0200288 | A1 | | 7/2014 | Jin et al. |

FOREIGN PATENT DOCUMENTS

| CA | 2250333 | | 4/1999 | |
| DE | 273846 | | 4/1912 | |
| DE | 2023293 | A1 * | 11/1971 | ............ D06M 13/41 |

OTHER PUBLICATIONS

English machine translation of (DE 2023293); generated Mar. 4, 2016.*

* cited by examiner

*Primary Examiner* — Michael Pepitone
(74) *Attorney, Agent, or Firm* — McNees Wallace & Nurick LLC

(57) ABSTRACT

Disclosed herein are methods of making polymerizable resins containing a 1,3,5-hexahydro-1,3,5-triazine moiety and dental compositions comprising such novel hydrolytic stable, polymerizable resins derived from 1,3,5-triacryloyl-hexahydro-1,3,5-triazine (TAT).

9 Claims, No Drawings

POLYMERIZABLE RESINS CONTAINING A 1,3,5-HEXAHYDRO-1,3,5-TRIAZINE MOIETY, METHODS OF MAKING, AND DENTAL COMPOSITIONS CONTAINING THE SAME

CROSS-REFERENCE TO RELATED APPLICATIONS

This application claims priority to, and the benefit of, U.S. Application No. 61/897,247 filed Oct. 30, 2013 which is hereby incorporated by reference in its entirety.

TECHNICAL FIELD

The present disclosure relates hydrolytic stable and water-soluble polymerizable resins containing a 1,3,5-hexahydro-1,3,5-triazine moiety, methods of preparing those resins, and dental compositions containing those resins.

BACKGROUND

Most dental resins are ester-based (meth)acrylate resin, which can be susceptible to hydrolytic degradation, especially when used in the presence of water and highly acidic conditions, such as self-etching adhesives. This in turn can impact the long-term performance or bounding durability. Therefore there is strong demand for hydrolytic stable polymerizable resins or additives such as hydrolytic stable polymerizable antibacterial resins or hydrolytic stable and water-soluble cross-linkers.

The polymerizable acrylamide resins are known for its hydrolytic stability and N-substituted acrylamide resins were also known for its improved water solubility. CA 2250333, U.S. Pat. Nos. 6,172,131 and 6,350,839 disclose hydrolysis-stable and polymerizable acrylphosphonic acids for use as dental adhesive monomers. DE 273846 discloses polymerizable phosphonic amides. U.S. 2010/0076157 discloses a method for producing a polymerizable amide containing both carboxylic and phosphoric groups.

SUMMARY

In one embodiment, a hydrolytic stable and water-soluble polymerizable resin containing a 1,3,5-hexahydro-1,3,5-triazine (TAT) moiety is disclosed. In another embodiment, a method of making such a resin is disclosed. In another embodiment a dental composition containing the resin is disclosed.

In one embodiment, the hydrolytic stable polymerizable resin comprises a TAT moiety with at least one acrylamide group.

In another embodiment, the hydrolytic stable polymerizable resin comprises a TAT moiety with at least an inorganic acidic group.

In yet another embodiment, the hydrolytic stable polymerizable resin comprises a TAT moiety with at least an imidazolium group.

In still another embodiment, the hydrolytic stable polymerizable resin comprises a TAT moiety with at least imidazole group.

Various features and advantages of the present invention will be apparent from the following more detailed description of exemplary embodiments that illustrate, by way of example, the principles of the invention.

DETAILED DESCRIPTION

It is highly desirable to have hydrolytic stable resins as hydrolytic stable, water-soluble additives, as hydrolytic stable adhesive monomers and hydrolytic stable antimicrobial resins. 1,3,5-triacryloyl-hexahydro-1,3,5-triazine (TAT) is a cyclic triacrylamide. TAT is an inexpensive, stable, and symmetrical compound that possesses three electron-deficient olefin groups. A variety of functionalized tripodal thioethers are readily synthesized via thiol-ene addition reaction. Highly water soluble derivatives are prepared via thiol-ene addition reaction.

TAT is a semi-crystalline solid and has limited miscibility in conventional dental resins. Therefore, it is highly desirable to selectively, chemically modify TAT so as to improve its solubility in conventional dental resins.

Exemplary embodiments are directed to novel hydrolytic stable, polymerizable resins derived from 1,3,5-triacryloyl-hexahydro-1,3,5-triazine (TAT), and more particularly to methods of increased selectivity via selective Michael addition for the formation of desirable mono- and di-substituted TAT based resins having the following general formula:

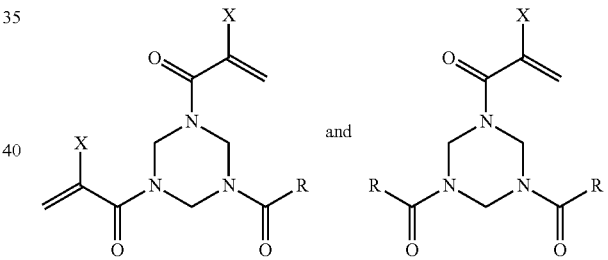

in which
X is H or $CH_3$,
R is $CH_2CH_2$—Y,
Y is —OR', —SR', —NHR", —NR'R", —NR'", or R'—OCO—CH—CO—R'
R' and R" independently or the same are linear or branched linear alkyl ($C_n$, n=1-18) with or without functional groups, and
R'" is a cyclic alkyl of $C_n$, (n=2-18) or a heterocyclic compound.

Functional groups for the linear or branched linear alkyl chains of R' and R" are of the general form of R'(R")—$Z_m$, in which m=1-3 and Z=—OH, —SH, —COOH, COOR'(R")(R'"), —OPO(OH)$_2$, —OPO(OR')(OH), —PO(OH)$_2$, —PO(OR')(OH), —OSO$_2$(OH), aromatics and substituted aromatics. Heterocyclic groups for —NR'" include imidazole and imidazole derivatives.

Scheme 1 illustrates a variety of different exemplary monofunctional resins that can be achieved.

Scheme 1: General Reaction of TAT derived Functional Resins

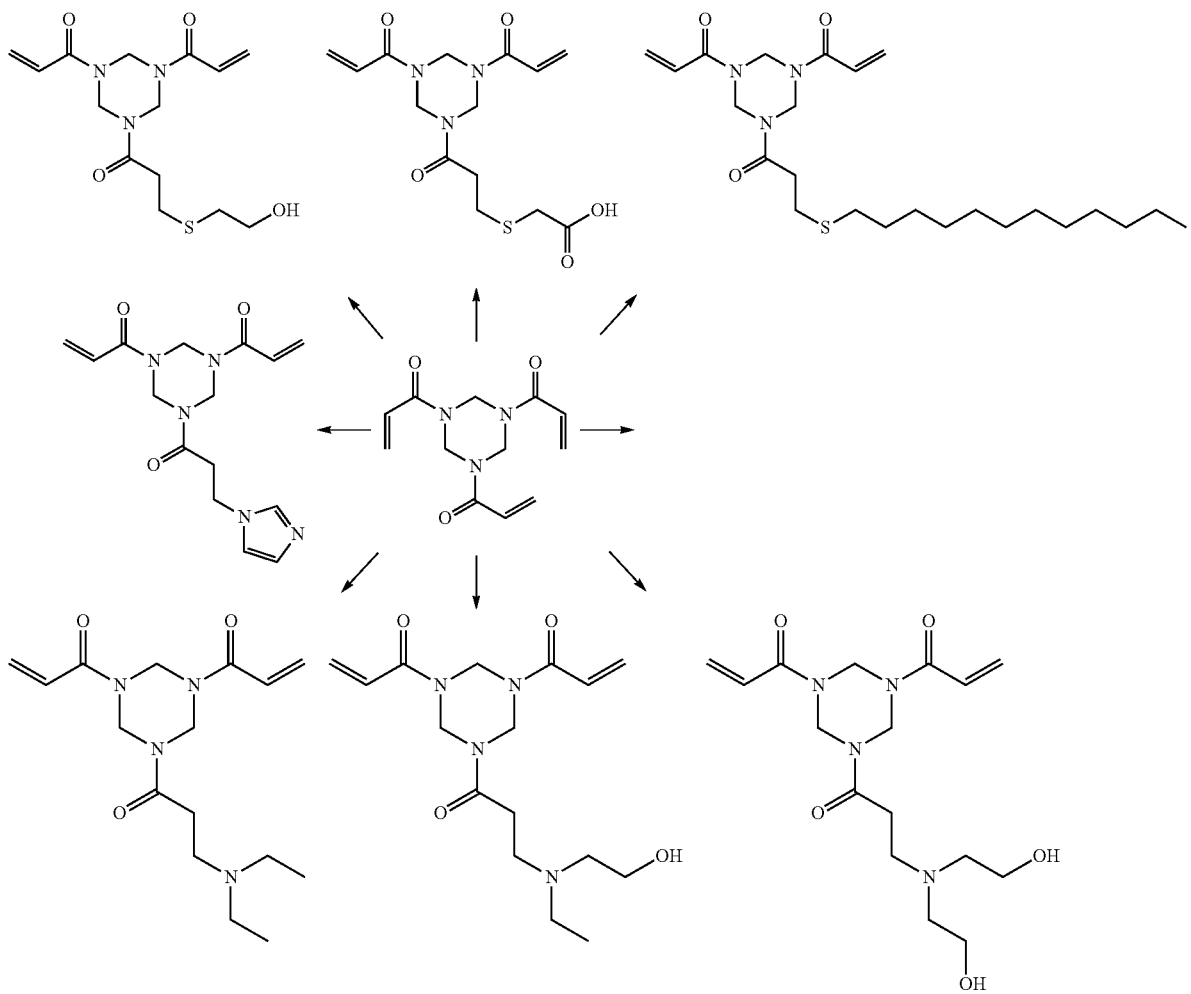

U.S. Pat. No. 8,747,831, incorporated here by reference, discloses a facile process developed to incorporate imidazole into polymerizable resin via Michael addition in the absence of a catalyst, which further readily may be converted into polymerizable imidazolium resins, which demonstrated remarkably high effectiveness in killing bacteria, including *S. mutans, S aureus*, and the like.

It was surprisingly found that imidazole-modified TAT demonstrated improved water-solubility, of which was identified as a mixture of unreacted TAT, monosubstituted TAT, disubstituted TAT and trisubstituted TAT. A new class of hydrolytic stable and water-soluble resins have been developed to better utilize the unique chemistry of the intrinsic cyclic acrylamide moiety from such TAT-derivatives and their improved water solubility.

Thus, one aspect of the present disclosure relates to method development, from which polymerizable resins are prepared respectively as hydrolytic stable and water-soluble polymerizable resins involving selective addition of Michael donors including thiols, amines, imidazole, etc. with TAT as the specific Michael acceptor under control conditions to yield primarily mono-substituted or di-substituted TAT with minimum fraction of unreacted TAT or tri-substituted TAT.

More particularly, exemplary embodiments lead to increased selectivity of the desirable polymerizable TAT (i.e., mono and di substituted TAT) by a solvent-based reaction process involves the step-wise addition of the Michael donor reactant compound in multiple divided portions, typically at least three, four, five or greater, over a period of time, usually at least an hour or more under stirring. It will be appreciated that the number of portions into which the total amount of reactant is split and the total time over which those portions are added may vary somewhat depending upon a variety of factors, including the specific Michael donor compound, the amount of TAT present, and the volume of solvent. If the reactant is added with TAT at the same time, controlled addition fails and selectivity shifts toward tri-substituted TAT, which is not polymerizable. Thus, exemplary embodiments slow the rate of dosing the reactant into the TAT system, especially in solution condition and low concentrations that favor the formation of mono- and di-substituted products, although it will be appreciated that some amount of tri-substituted TAT as well as unreacted TAT is still present.

Furthermore, the versatility of TAT-modification as illustrated in Scheme 1 also allows incorporating a variety of secondary functional groups like hydroxyl, carboxyl, etc. from which new polymerizable resins with a built-in cyclic, N-substituted alkylacrylamide moiety can be readily prepared. Functional groups readily varied from thiols, amines hydroxyl, acids etc., from which further derivatives can be prepared accordingly, such as phosphoric acid, imidazole, imidazolium or ester, carbonate, urethane-derived resins.

Preferably, such hydrolytic stable TAT-derived polymerizable resins are soluble water or a mixture of water and another one or more organic solvents. In some embodiments the organic water-soluble solvent is water mixed with ethanol, propanol, butanol, acetone, and/or methyl ethyl ketone.

In some embodiments, the such hydrolytic stable TAT-derived polymerizable resin contains an inorganic acidic moiety selected from a phosphonic acid moiety or a sulfonic acid moiety. In a preferred embodiment, hydrolytic stable TAT-derived polymerizable resins contain at least one imidazole moiety to impart acid neutralizing capability. In another preferred embodiment, hydrolytic stable TAT-derived polymerizable resins contain at least one moiety selected from imidazolium for capability to killing microbes/bacteria. It will be appreciated that some in some cases, a composition may be formulated having a combination of such resins to impart a combination of the functions.

Accordingly, exemplary embodiments are also directed to a variety of dental compositions comprising such hydrolytic stable TAT-derived polymerizable resins or additives that includes a hydrolysis stable polymerizable resin that comprises TAT moiety with at least one acrylamide group, a hydrolysis stable polymerizable resin that comprises TAT moiety with at least an inorganic acidic group, a hydrolysis stable polymerizable resin that comprises TAT moiety with at least an imidazolium group, a hydrolysis stable polymerizable resins that comprises TAT moiety with at least imidazole group, and combinations thereof.

In one embodiment disclosed a hydrolytic stable TAT-derived polymerizable resin includes cyclic N-substituted alkylacrylamide and contain at least one polymerizable group (acrylamide) and an inorganic acidic moiety and/or a charged moiety like imidazolium.

In some cases, a composition may be formulated with up to 10 to 20% by weight or greater of the TAT-derived resins with the balance being made up of conventional resins, including those known for use in forming dental composite compositions. Such additional resins to which TAT-derived resins may be added include, but are not limited to, acrylate resins and methacrylate resin or methacrylate/acrylate hybrid resins. Examples of specific acrylate resins include ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and diacrylate, ethyleneglycol diacrylate, polyethyleneglycol diacrylate, neopentyl glycol diacrylate, trimethylolpropane triacrylate, mono-, di-, tri-acrylate, mono-, di-, tri-, and tetra-acrylates of pentaerythritol and dipentaerythritol, 1,3-butanediol diacrylate, 1,4-butanedioldiacrylate, 1,6-hexane diol diacrylate, 2,2% bis[3(4-phenoxy)-2-hydroxypropane-1-acrylate]propane, 2,2'bis(4-acryloxyphenyl)propane, 2,2'-bis[3(4-phenoxy)-2-hydroxypropane-1-acrylate]propane, dipentaerthritol pentaacrylate esters and dipentaerthritol pentaacrylate esters. Examples of specific conventional methacrylate resins include methacrylates, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (BisGMA), glycerol mono- and di-methacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentaerythritol and dipentaerythritol, 1,3-butanediol dimethacrylate, 1,4-butanediol dimethacrylate, Bis[2-(methacryloyloxy)ethyl]phosphate (BisMEP), 1,6-hexanediol dimethacrylate, 2-2'-bis(4-methacryloxyphenyl)propane, 2,2'-bis[4(2-hydroxy-3-methacryloxy-phenyl)]propane, 2,2'bis[4(2-hydroxy-3 acryloxyphenyl)propane, 2,2'-bis(4-methacryloxyethoxyphenyl) propane, 2,2'-bis(4-acryloxyethoxyphenyl)propane, 2,2'-bis (4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-dydroxypropane-1-methacrylate]propane.

In some embodiments, the combination of resins may be tailored to achieve a desired index of refraction for the dental composition. It was also discovered that TAT-derived resins such as those produced by TAT-based Michael thiol addition reactions results in non-aromatic polymerizable resins with a high refractive index via partial thiol addition. Thus, TAT-derivatives can be readily prepared via a facile thiol-ene addition reaction to yield a resin with a higher index of refraction that is, in some cases, even higher than aromatic resins.

In exemplary embodiments that are dental composite compositions, the composition may contain from about 5% to about 95% by weight resin, initiators and other additives in amounts of from about 0.001% to about 5.0% percent by weight of the dental composition, and a plurality of filler particles having a size of from about 10 nm to about 100 micron of the dental composition, the filler particles typically being present from about 5% by weight, up to about 95% by weight, typically from about 40% to about 80%. Of the resin amount, up to about 20% weight, typically up to about 10% by weight of the resin is TAT-derived resin, such that the overall amount of the TAT-derived resin in the total dental composite composition is less than 10% by weight, in some cases from about 1% to 2% by weight and in other cases from about 2% to about 5% by weight of the TAT-derived resin.

The fillers of the composition can be any suitable filler materials, including glass powder of various particles sizes and one or more fluoride releasing agents. Glass particles not only improve the physical and mechanical properties of the composition, but also serve as a base for the acid-base reaction. The powder component may also contain other filler materials such as barium, Aerosil 200, pigments, silica, alumina, aluminum fluoride, calcium fluoride, sodium fluoride, aluminum phosphate, calcium, strontium, zinc, sodium, potassium, lanthanum, alumino-silicates, other metal oxides, metal fluorides and metal phosphates and combinations thereof.

The initiators of the compositions disclosed herein are also included to permit photo or chemical initiation of curing, which could be incorporated into either the liquid component or the powder component. The formulation may additionally contain a co-initiator to accelerate the curing process. In the preferred embodiment, both a light-curing initiator camphorquinone (CQ) and a self-curing initiator (e.g., BPO) are used. A curing inhibitor, such as BHT, may also be included in the composition in order to have a more controlled curing time and shelf life.

Exemplary embodiments are further described and illustrated with respect to the following examples which are presented by way of explanation, not of limitation.

EXAMPLES

A variety of hydroxyl-terminated TAT derivatives were prepared via Michael addition of TAT and diethanol amine (DEA) by using a microwave-assisted process. The reaction pathway is illustrated below as Scheme 2:

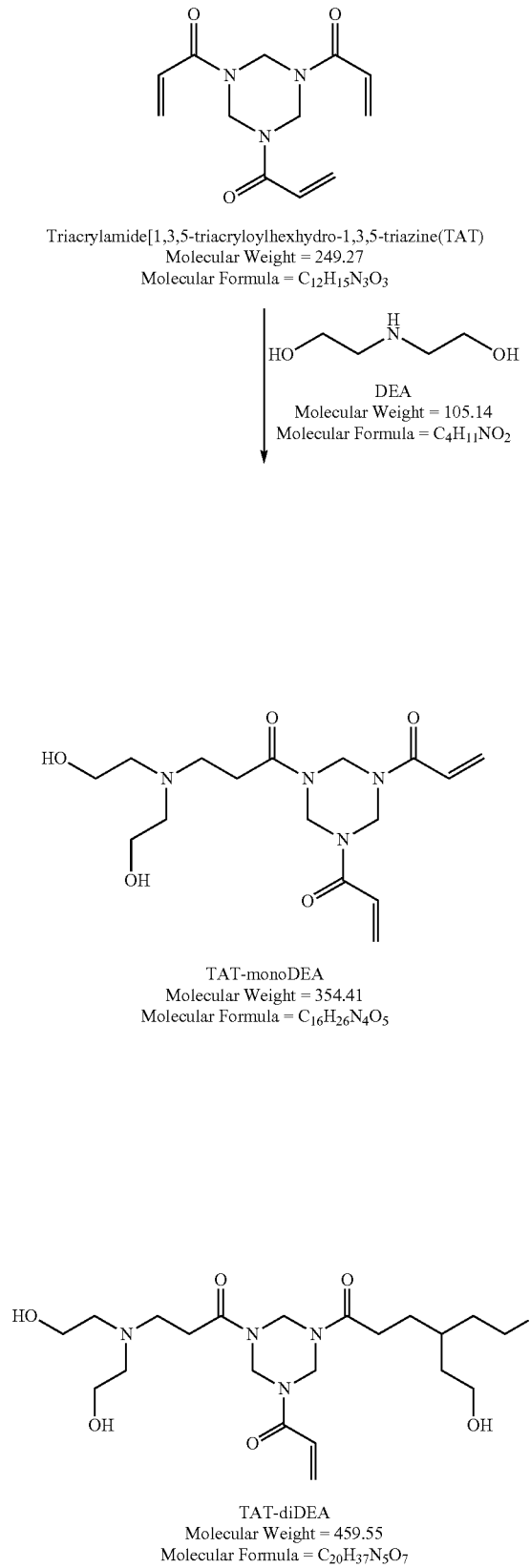

Triacrylamide[1,3,5-triacryloylhexhydro-1,3,5-triazine(TAT)
Molecular Weight = 249.27
Molecular Formula = C$_{12}$H$_{15}$N$_3$O$_3$ DEA
Molecular Weight = 105.14
Molecular Formula = C$_4$H$_{11}$NO$_2$ TAT-monoDEA
Molecular Weight = 354.41
Molecular Formula = C$_{16}$H$_{26}$N$_4$O$_5$ TAT-diDEA
Molecular Weight = 459.55
Molecular Formula = C$_{20}$H$_{37}$N$_5$O$_7$

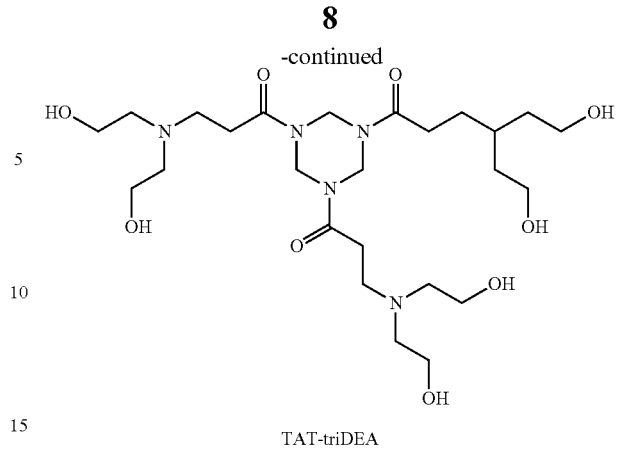

TAT-triDEA
Molecular Weight = 564.68
Molecular Formula = C$_{24}$H$_{48}$N$_6$O$_9$ Example 1

To a 25 ml vial, 0.02 mol (5.00 g) of TAT, 0.025 mol (2.6 g) of DEA and 10 g of acetonitrile were added. The composition was mixed for 10 minutes under magnetic stirring at room temperature resulting in formation of a slurry. A sealed vial of the slurry was placed into the reaction chamber of a microwave synthesizer (Initiator Plus from Biotage). With premix 1 min/room temperature, followed by 100° C. for 5 min, a clear solution was formed. After 30 min additional mixing at room temperature, a hazy solution is developed. Following solvent removal, a semi-crystalline resin resulted.

Example 2

To a 25 ml vial, 0.02 mol (5.14 g) of TAT, 0.035 mol (3.85 g) of DEA and 7 g of acetonitrile were added. The composition was mixed for 10 minutes under magnetic stirring at room temperature resulting in formation of a slurry. A sealed vial of the slurry was placed into the reaction chamber of a microwave synthesizer (Initiator Plus from Biotage). With premix 1 min/room temperature, followed by 100° C. for 5 min, a clear solution was formed. After 60 min mixing at room temperature, a clear solution remained. Following solvent removal, a clear resin resulted.

Example 3

To a 25 ml vial, 0.02 mol (5.09 g) of TAT, 0.04 mol (4.19 g) of DEA and 6 g of acetonitrile were added. The composition was mixed for 10 minutes under magnetic stirring at room temperature resulting in formation of a slurry. A sealed vial of the slurry was placed into the reaction chamber of a microwave synthesizer (Initiator Plus from Biotage). With premix 1 min/room temperature, followed by 100° C. for 5 min, a clear solution was formed. After 60 min mixing at room temperature, a clear solution remained. Following solvent removal, a clear resin resulted.

Example 4

To a 25 ml vial, 0.02 mol (5.12 g) of TAT, 0.065 mol (6.81 g) of DEA and 6 g of acetonitrile were added. The composition was mixed for 10 minutes under magnetic stirring at room temperature resulting in formation of a slurry. A sealed vial of the slurry was placed into the reaction chamber of a microwave synthesizer (Initiator Plus from Biotage). With premix 1 min/room temperature, followed by 100° C. for 5 min, a clear solution was formed. After 30 min mixing at room temperature, a hazy solution developed. Following solvent removal, a clear resin resulted.

A sample of each of the examples was then subjected to further characterization and testing, including by NMR, along with pure TAT. The results are summarized in Table 1, which illustrates, among other things, that the increased amounts of DEA improved the solubility:

TABLE 1

Composition Effect on Solubility of Hydroxy-terminated TAT Derivatives

| Resin | TAT/ DEA (mole/ mole) | Hac/ Hcore calcu- lated | Hac/Hcore measured by 1H NMR | Resin's Physical Form | Solubility in water/ EtOH (1:1) @ 25% w/w |
|---|---|---|---|---|---|
| Parent Sample (TAT) | | 1.5 | NA | crystal | insoluble |
| Example 1 | 0.02/0.025 | 1.0 | 1.01 | semi-crystalline | insoluble |
| Example 2 | 0.02/0.035 | 0.5 | 0.73 | hazy liquid | soluble |
| Example 3 | 0.02/0.040 | 0.5 | 0.72 | clear liquid | soluble |
| Example 4 | 0.02/0.065 | 0 | 0.20 | clear liquid | soluble |

Hac: integral TAT-acrylamide intensity
Hcore: integral TAT-methylene intensity

Example 5

A polymerizable imidazolium resin derived from reaction of bromododecane and the adduct of imidazole and TAT was prepared using a two-pot, two-step process.

Into a 500 ml three-neck round flask, 0.20 mol (50.30 g) of TAT, 0.24 g of dithanolamine (DEA) and 200 g of methanol were added under mixing with a mechanical stirrer for 10 min. Under mixing, 20.4 g of imidazole crystal powder was added in portions over a 90 min span. The reaction was then kept at RT overnight. The result was a clear solution, from which solvent was removed via Rotavapo under reduced pressure to produce a liquid resin. The result was sampled for NMR analysis to monitor reaction progress.

The 63.5 g of the resultant resin was dissolved in 200 g of acetonitrile in a 500 ml three-neck round flask, after which 0.255 mol (65 g) of bromododecane was charged into the flask. The reaction was maintained at 40° C. for five days. The product was regularly sampled for use in NMR analysis to monitor the conversion. A clear, high viscosity resin resulted that was precipitated in hexane to remove unreacted bromododecane and solvent resulting in a wax-like resin was then readily dissolved in methylene dichloride. That solvent was then removed via Rotavapor under reduced pressure to produce a solid resin.

Schemes 3 through 5 illustrate the transition of TAT to mono-, di- and tri-substituted resin of the first step of Example 5, while Scheme 6 illustrates the subsequent reaction step to yield an imidazolium resin.

Scheme 3: Reaction for Mono-substituted Imidazole Adduct to TAT

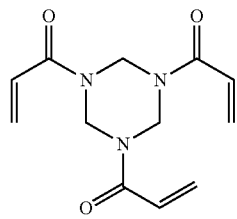

Triacrylamide[1,3,5-triacryloylhexhydro-1,3,5-triazine(TAT)
Molecular Weight = 249.27
Molecular Formula = $C_{12}H_{15}N_3O_3$

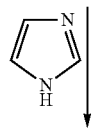

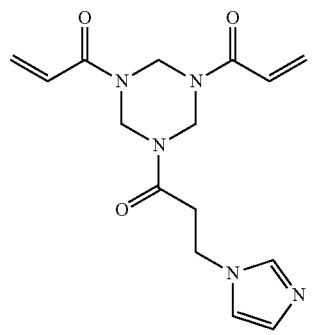

Scheme 4: Reaction for Di-substituted Imidazole Adduct to TAT

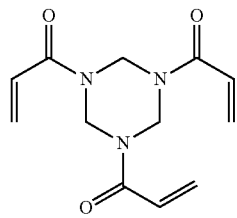

Triacrylamide[1,3,5-triacryloylhexhydro-1,3,5-triazine(TAT)
Molecular Weight = 249.27
Molecular Formula = $C_{12}H_{15}N_3O_3$

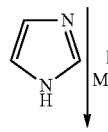 Imidazole
Molecular Weight = 68.08
Molecular Formula = $C_3H_4N_2$

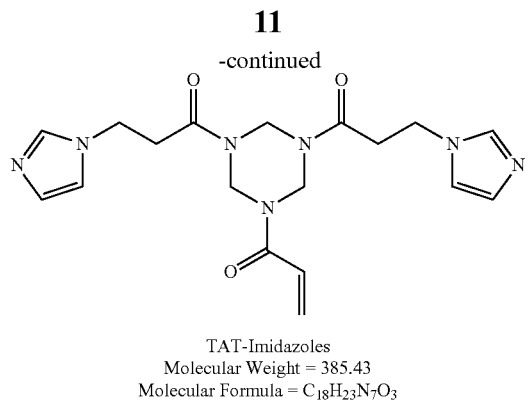

TAT-Imidazoles
Molecular Weight = 385.43
Molecular Formula = $C_{18}H_{23}N_7O_3$ Scheme 5: Reaction for All-substituted Imidazole Adduct to TAT

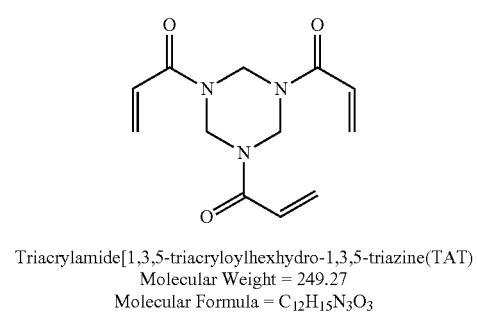

Triacrylamide[1,3,5-triacryloylhexhydro-1,3,5-triazine(TAT)
Molecular Weight = 249.27
Molecular Formula = $C_{12}H_{15}N_3O_3$

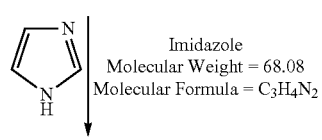

Imidazole
Molecular Weight = 68.08
Molecular Formula = $C_3H_4N_2$

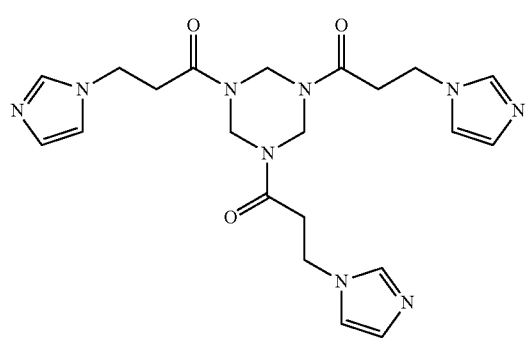

TAT-Imidazoles
Molecular Weight = 453.51
Molecular Formula = $C_{21}H_{27}N_9O_3$ Scheme 6: Reaction Scheme to TAT-based Polymerizable Imidazolium Resin (C12Im-TAT)

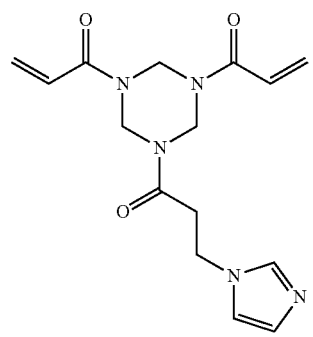

TAT-IM-I

↓

C12B-TAT-IM-I

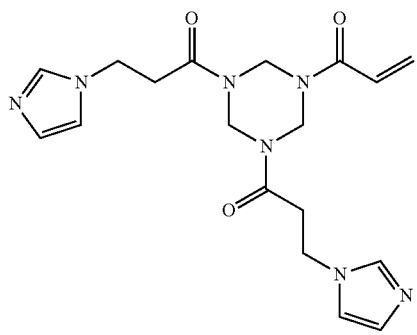

TAT-IM-II

↓

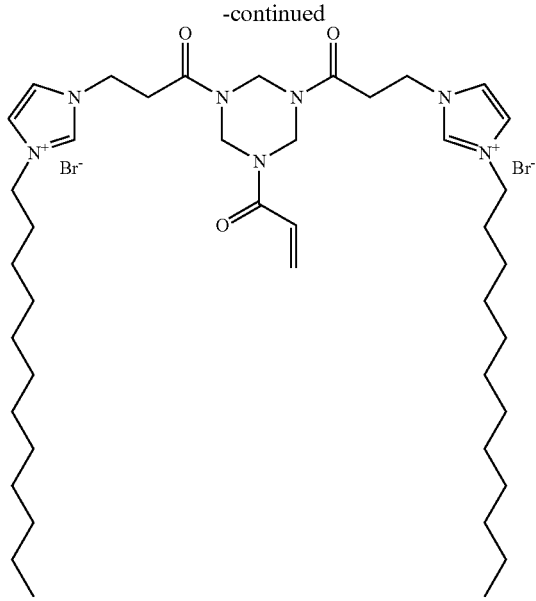

C12B-TAT-IM-II

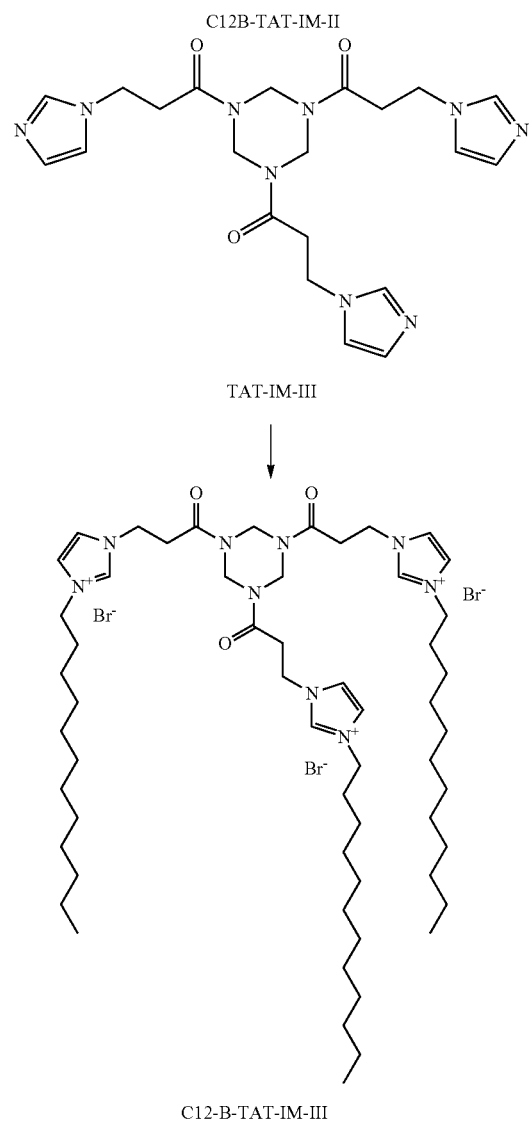

TAT-IM-III

↓

C12-B-TAT-IM-III

Examples 6-8

Examples 6 through 8 were created as formulated dental compositions using the imidazolium resin prepared in Example 5, an isosorbide resin (of the type disclosed in U.S. 2014/0200288, which is hereby disclosed by reference), triethyleneglycol dimethacrylate (TEGDMA), initiator (camphorquinone (CQ), ethyl-4-(dimethylamino)benzoate (EDAB), and/or ethyl 2,4,6-trimethylbenzoylphenylphosphinate (LTPO)), and 2,6-di(tert-butyl)-4-methylphenol (BHT) as an inhibitor. The specific composition of each example is shown subsequently in Table II.

Examples 9-11

Example 9 through 11 were created as formulated composites comprising the formulated resins Example 6, Example 7, and Example 8, respectively, along with a filler. The specific compositions of each, along with certain measured mechanical properties following curing using different light sources as noted, are shown in Table IIIa.

Example 12

A polymerizable imidazolium resin derived from reaction of bromododecane and the adduct of imidazole and TAT was prepared using a one-pot, two-step process.

Into a 500 ml three-neck round flask, 0.20 mol (50.30 g) of TAT, 0.25 g of dithanolamine (DEA) and 205 g of acetonitrile were added. Under magnetic stirring, 0.30 mol (20.40 g) of imidazole crystal powder was added in four portions within a 150 min span. Then the reaction was kept at room temperature overnight. Sampling for NMR analysis showed that 85% of conversion was reached.

To this system, 0.30 mol (74.8 g) of bromododecane was added, forming a hazy solution. The reaction was maintained at 40° C. for seven days. A gel-like, inhomogeneous liquid resin resulted, which was precipitated in hexane and dissolved in methylene dichloride. All solvent was removed via Rotavapor under reduced pressure to yield 133 g of solid resin.

Examples 13-15

Examples 13 through 15 were created as formulated dental compositions using the imidazolium resin prepared in Example 12, isosorbide resin, TEGDMA, initiator (CQ, EDAB and/or LTPO), and BHT as an inhibitor. The specific composition of each example is shown subsequently in Table II.

Examples 16-18

Examples 16 through 18 were created as formulated composites comprising the formulated resins of Example 13, Example 14, and Example 15, respectively, along with a filler. The specific compositions of each, along with certain measured mechanical properties following curing using different light sources as noted, are shown in Table IIIb.

Example 19

A polymerizable imidazolium resin derived from reaction of bromohexane and the adduct of imidazole and TAT was prepared using a one-pot, two-step process.

Into a 250 ml three-neck round flask, 0.05 mol (12.46 g) of TAT, and 100 g of acetonitrile were added. Under a magnetic stirring, 0.105 mol (7.15 g) of imidazole crystal powder was added in portions within a 120 min span. Then the reaction was kept at room temperature overnight. Sampling for NMR analysis showed that 85% of conversion was reached.

To this system, 0.105 mol (26.46 g) of bromohexane was added, forming a hazy solution. The reaction was maintained at 40° C. for five days. An inhomogeneous liquid resin resulted, which was then precipitated in hexane and dissolved in methylene dichloride. All solvent was removed via Rotavapor under reduced pressure to yield a solid resin.

The reaction for Example 19 is shown in Scheme 7.

Scheme 7: Reaction Scheme to TAT-based Polymerizable Imidazolium Resin (C6Im-TAT)

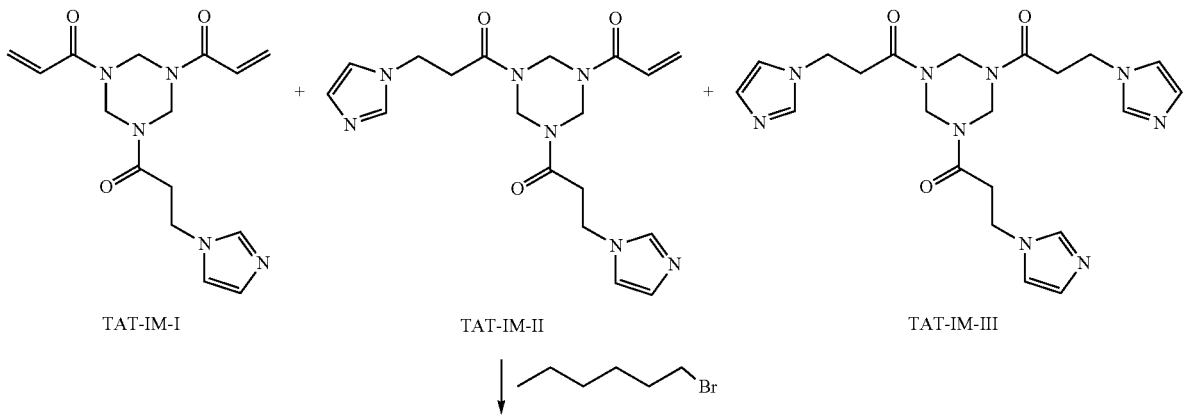

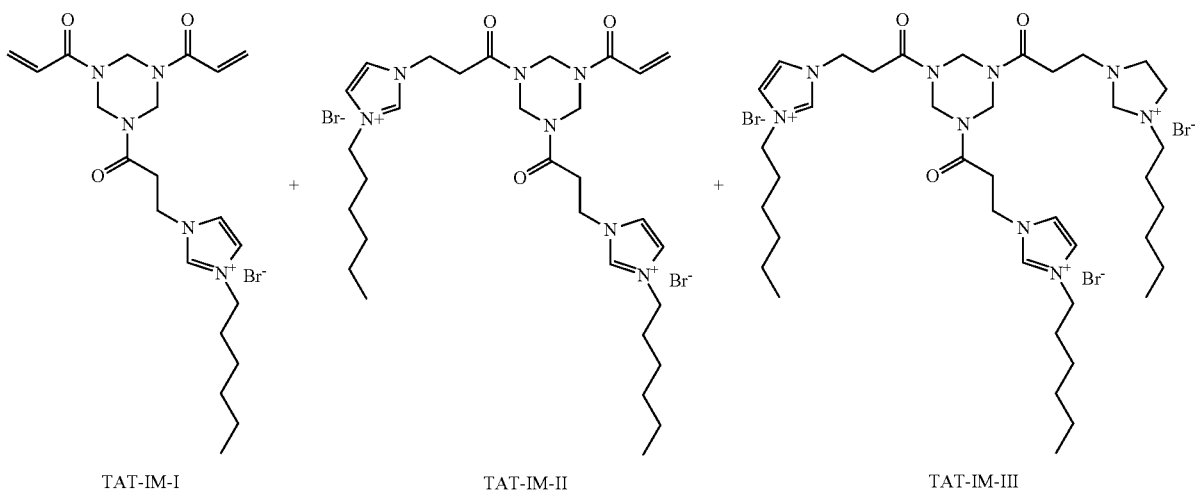

Examples 20-22

Examples 20 through 22 were created as formulated dental compositions using the imidazolium resin prepared in Example 19, isosorbide resin, TEGDMA, initiator (CQ, EDAB and/or LTPO), and BHT as an inhibitor. The specific composition of each example is shown subsequently in Table II.

Examples 23-25

Examples 23 through 25 were created as formulated composites comprising the formulated resins of Example 20, Example 21, and Example 22, respectively, along with a filler. The specific compositions of each, along with certain measured mechanical properties following curing using different light sources as noted, are shown in Table IIIc.

TABLE II

Compositions and Properties of Formulated Resins

|  | Isosorbide Resin wt % | TEGDMA wt % | Ex. 5 wt % | Ex. 12 wt % | Ex. 19 wt % | CQ wt % | EDAB wt % | LTPO wt % | BHT wt % |
|---|---|---|---|---|---|---|---|---|---|
| Example 6 | 79.53 | 9.94 | 9.94 | — | — | 0.164 | 0 | 0.398 | 0.028 |
| Example 7 | 79.61 | 9.95 | 9.95 | — | — | 0.164 | 0.298 | 0 | 0.028 |
| Example 8 | 84.25 | 9.91 | 4.95 | — | — | 0.164 | 0.299 | 0.399 | 0.028 |
| Example 13 | 79.53 | 9.94 | — | 9.94 | — | 0.164 | 0 | 0.398 | 0.028 |
| Example 14 | 79.61 | 9.95 | — | 9.95 | — | 0.164 | 0.298 | 0 | 0.028 |
| Example 15 | 84.25 | 9.91 | — | 4.95 | — | 0.164 | 0.299 | 0.399 | 0.028 |
| Example 20 | 79.53 | 9.94 | — | — | 9.94 | 0.164 | 0 | 0.398 | 0.028 |
| Example 21 | 79.61 | 9.95 | — | — | 9.95 | 0.164 | 0.298 | 0 | 0.028 |
| Example 22 | 84.25 | 9.91 | — | — | 4.95 | 0.164 | 0.299 | 0.399 | 0.028 |

TABLE IIIa

Compositions and Properties of Composites Containing Antibacterial Resin

| Composite Compositions | Example 9 | Example 10 | Example 11 |
|---|---|---|---|
| Resin Blend | Example 6 19.84% | Example 7 19.60% | Example 8 19.43% |
| Filler Blend | 80.16% | 80.40% | 80.57% |
| Stress @ 60 min (QHL Blue) MPa | 2.43 | 1.86 | 2.31 |
| Halogen Light Compr. St.(MPa) | 300 ± 30 | 290 ± 30 | 305 ± 20 |
| Compr. Mod.(MPa) | 6140 ± 400 | 6100 ± 300 | 6500 ± 300 |
| Halogen Light Flex. St.(MPa) | 125 ± 7 | 30 | 141 ± 10 |
| Flex. Mod.(MPa) | 9860 ± 720 | 117 ± 10 | 12500 ± 680 |
|  |  | 9960 ± 400 |  |
| LED Light Compr. St.(MPa) | 324 ± 50 | 356 ± 40 | 392 ± 20 |
| Compr. Mod.(MPa) | 5660 ± 250 | 6310 ± 300 | 6700 ± 200 |
| LED Light Flex. St.(MPa) | 101 ± 20 | 133 ± 10 | 144 ± 20 |
| Flex. Mod.(MPa) | 6100 ± 400 | 6100 ± 300 | 6500 ± 300 |

TABLE IIIb

Compositions and Properties of Composites Containing Antibacterial Resin

| Composite Compositions | Example 16 | Example 17 | Example 18 |
|---|---|---|---|
| Resin Blend | Example 13 19.84% | Example 14 19.60% | Example 15 19.43% |
| Filler Blend | 80.16% | 80.40% | 80.57% |
| Stress @ 60 min (QHL Blue) MPa | 2.10 | 2.11 | 2.46 |
| Halogen Light Compr. St.(MPa) | 300 ± 20 | 303 ± 15 | 302 ± 25 |
| Compr. Mod.(MPa) | 6550 ± 150 | 6200 ± 250 | 6350 ± 350 |
| Halogen Light Flex. St.(MPa) | 115 ± 8 | 125 ± 7 | 146 ± 4 |
| Flex. Mod.(MPa | 9600 ± 750 | 9400 ± 250 | 12300 ± 830 |
| LED Light Compr. St.(MPa) | 260 ± 10 | 286 ± 30 | 300 ± 20 |
| Compr. Mod.(MPa) | 5250 ± 100 | 5610 ± 500 | ± |
| LED Light Flex. St.(MPa) | 92 ± 9 | 129 ± 12 | 136 ± 13 |
| Flex. Mod.(MPa) | 5650 ± 500 | 10700 ± 710 | 11260 ± 370 |

TABLE IIIc

Compositions and Properties of Composites Containing Antibacterial Resin

| Composite Compositions | Example 23 | Example 24 | Example 25 |
|---|---|---|---|
| Resin Blend | Example 20 19.84% | Example 21 19.60% | Example 22 19.43% |
| Filler Blend | 80.16% | 80.40% | 80.57% |
| Stress @ 60 min (QHL Blue) MPa | 2.45 | 1.98 | 2.55 |

TABLE IIIc-continued

Compositions and Properties of Composites Containing Antibacterial Resin

| Composite Compositions | Example 23 | Example 24 | Example 25 |
|---|---|---|---|
| Halogen Light Compr. St.(MPa) | 307 ± 12 | 300 ± 10 | 329 ± 10 |
| Compr. Mod.(MPa) Halogen Light | 6040 ± 320 | 6140 ± 190 | 6540 ± 100 |
| Flex. St.(MPa) | 132 ± 6 | 146 ± 7 | 157 ± 5 |
| Flex. Mod.(MPa | 10440 ± 510 | 11120 ± 360 | 12430 ± 1300 |
| LED Light Compr. St.(MPa) | 255 ± 10 | 280 ± 15 | 270 ± 30 |
| Compr. Mod.(MPa) LED Light | 4890 ± 200 | 5830 ± 450 | 5560 ± 560 |
| Flex. St.(MPa) | 103 ± 6 | 134 ± 6 | 137 ± 10 |
| Flex. Mod.(MPa) | 6530 ± 660 | 10110 ± 680 | 10700 ± 760 |

Additional examples include a polymerizable phosphoric acid resin derived from adduct of (ethylamino) ethanol (EAE) and 1,3,5-triacryloylhexahydro-1,3,5-triazine (TAT) prepared using a two-pot, two-step process as illustrated in Schemes 8 and 9.

Scheme 8: Reaction for Mono-substituted EAE Adduct to TAT

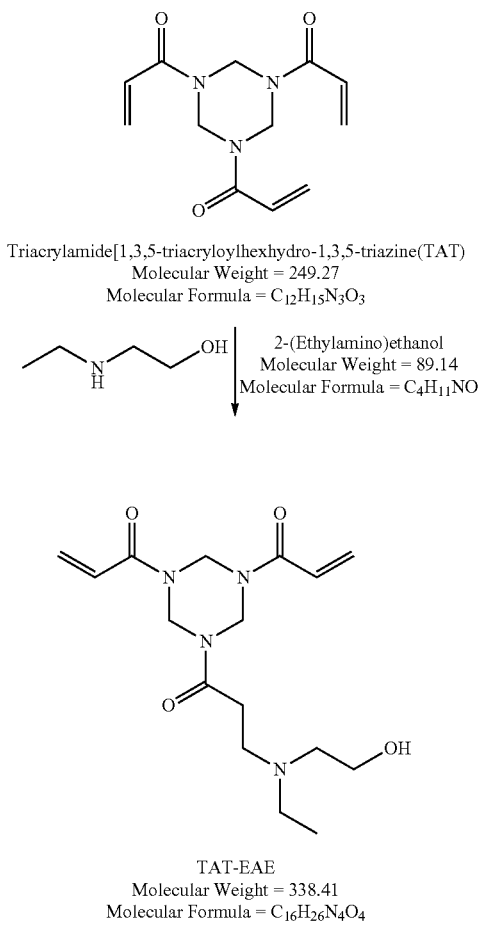

Scheme 9: Reaction for all substituted EAE Adduct to TAT

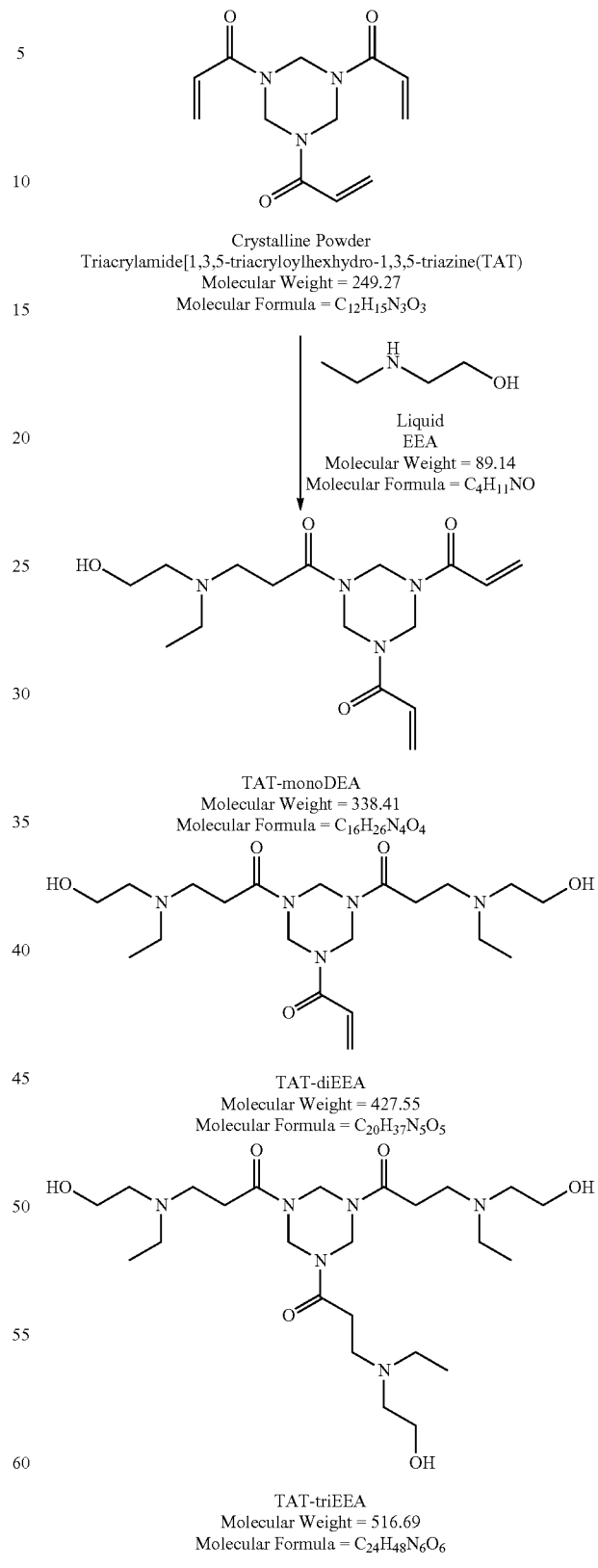

Other examples included hydroxyl-terminated TAT-derivatives as described in Examples 1-4 used as a precursor for a variety of polymerizable phosphoric acid with a general procedure as follows.

Into a 1000 ml four-neck resin kettle equipped with chiller of −20° C. and dry air inlet, a mechanical stirrer, and 200 ml additional funnel, 0.62 mol (95.06 g) of oxiphosphorous trichloride and 200 ml of THF were added. Then a solution of hydroxyl-terminated precursor, 0.63 mol (62.7 g) of TEA and 200 ml methylene dichloride (not a completely clear solution) was added drop-wise so as to maintain the reaction temperature below −15° C. during the 150 min addition duration. Then keep the reaction for additional 120 min at −20° C. and then stop chiller and have the reaction temperature warm up for additional 60 min. The cold slurry was filtered to remove the TEA salt crystal. 24.5 g of deionized water was added to the filtrate solution and was allowed to settle at room temperature overnight. Two layers formed—a clear top layer was decanted and the bottom layer was collected and air-dried to yield a clear liquid polymerizable phosphoric acid resin.

Still other resins can be formulated consistent with the methods described herein, as illustrated by the reactions shown in Schemes 10 through 16.

Scheme 10: Reaction for Mono-substituted EAB Adduct to TAT

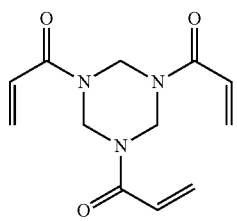

Triacrylamide[1,3,5-triacryloylhexhydro-1,3,5-triazine(TAT)
Molecular Weight = 249.27
Molecular Formula = $C_{12}H_{15}N_3O_3$

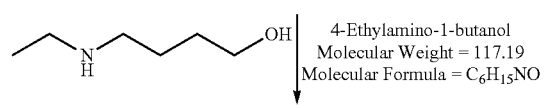

4-Ethylamino-1-butanol
Molecular Weight = 117.19
Molecular Formula = $C_6H_{15}NO$

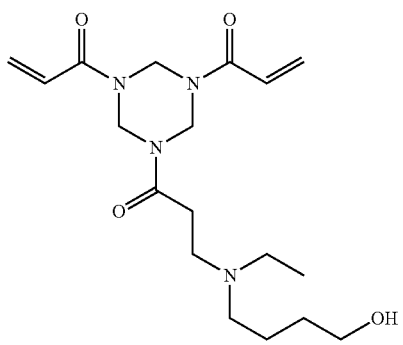

TAT-EAB
Molecular Weight = 336.46
Molecular Formula = $C_{18}H_{30}N_4O_4$

Scheme 11: Reaction for Mono-substituted EPA Adduct to TAT

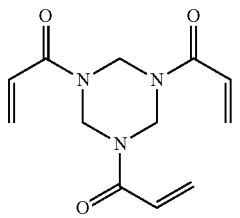

Triacrylamide[1,3,5-triacryloylhexhydro-1,3,5-triazine(TAT)
Molecular Weight = 249.27
Molecular Formula = C12H15N3O3

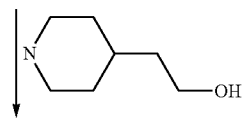

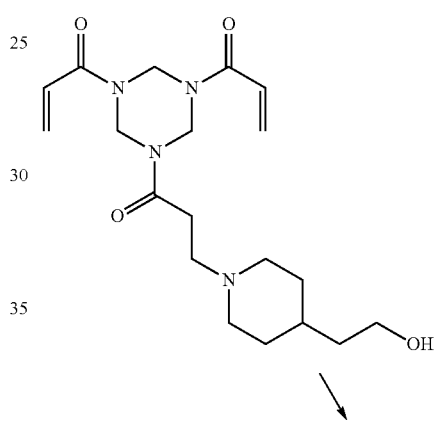

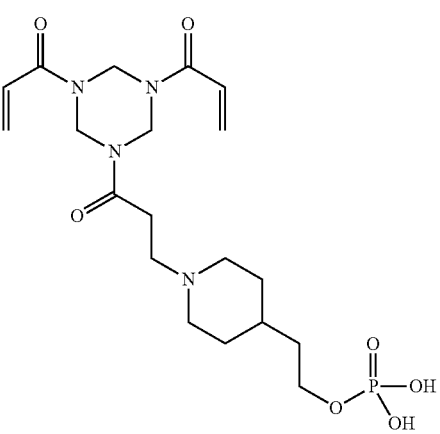

Scheme 12: Reaction for All-substituted EAZ Adduct to TAT
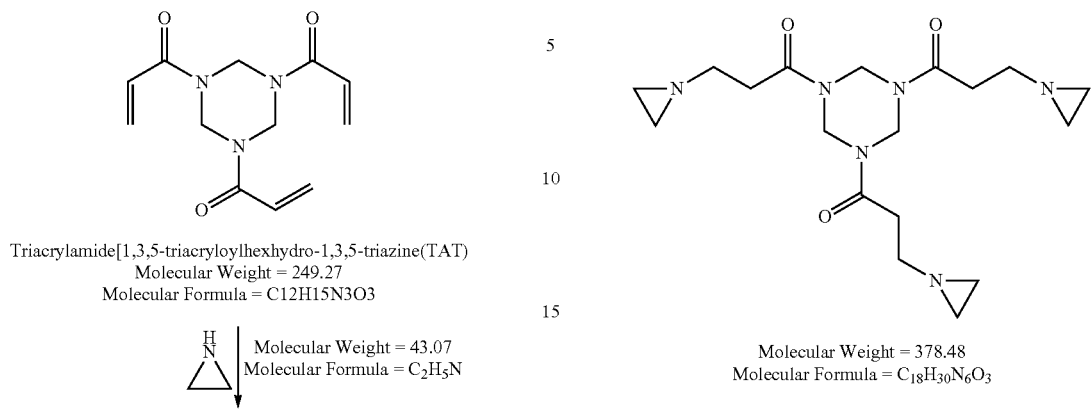
Triacrylamide[1,3,5-triacryloylhexhydro-1,3,5-triazine(TAT)
Molecular Weight = 249.27
Molecular Formula = C12H15N3O3
Molecular Weight = 43.07
Molecular Formula = $C_2H_5N$
Molecular Weight = 378.48
Molecular Formula = $C_{18}H_{30}N_6O_3$
Scheme 13: Reaction to Adhesive Monomer from All-substituted EAD Adduct to TAT
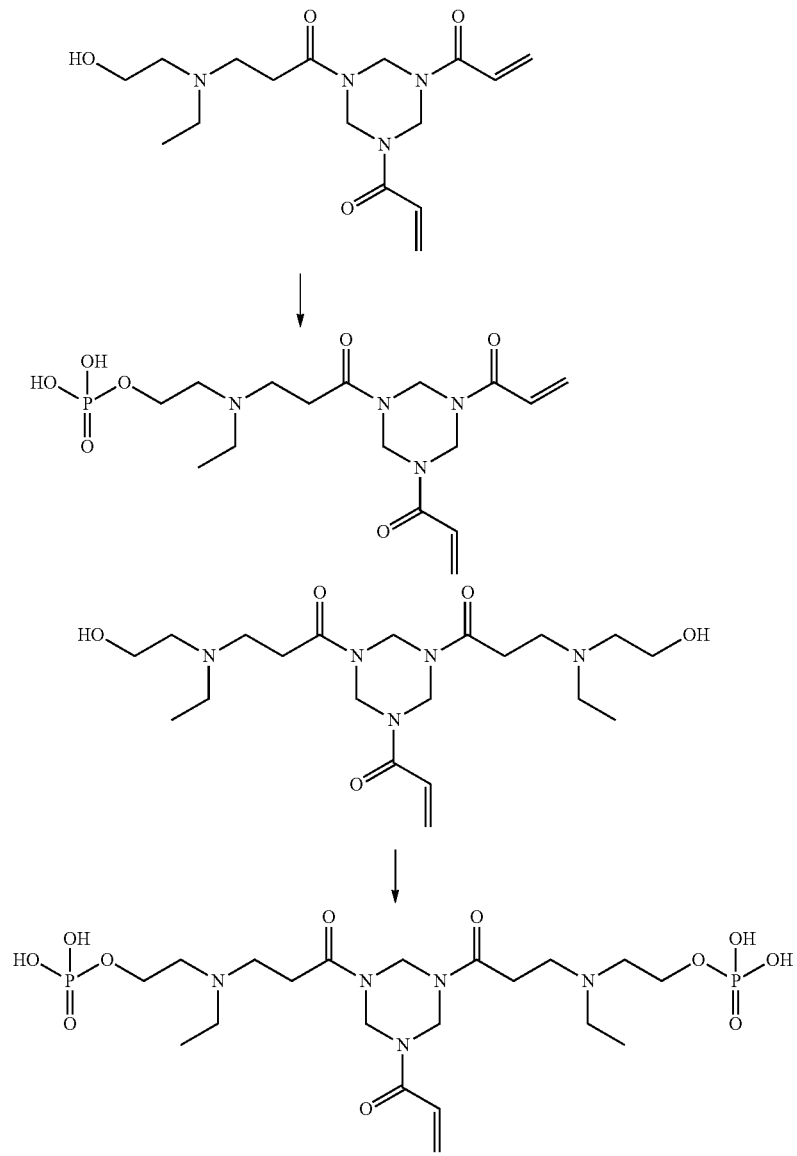

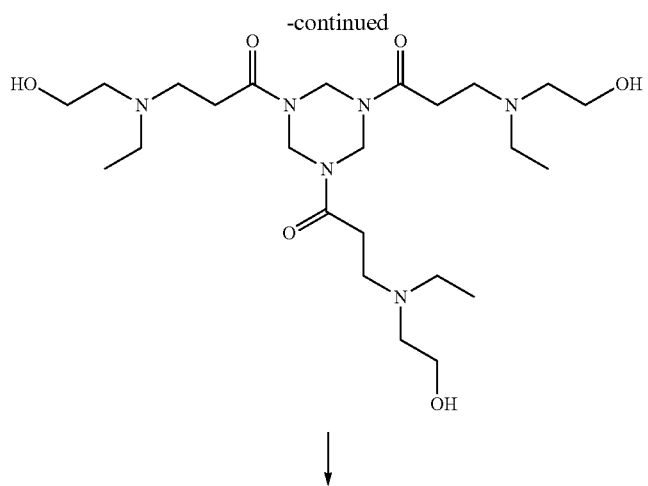
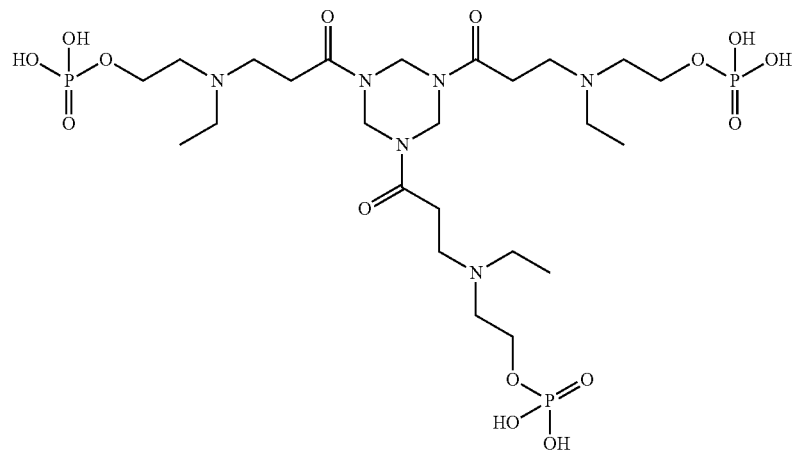
Scheme 14: Reaction to Adhesive Monomer from All-substituted GLT Adduct to TAT
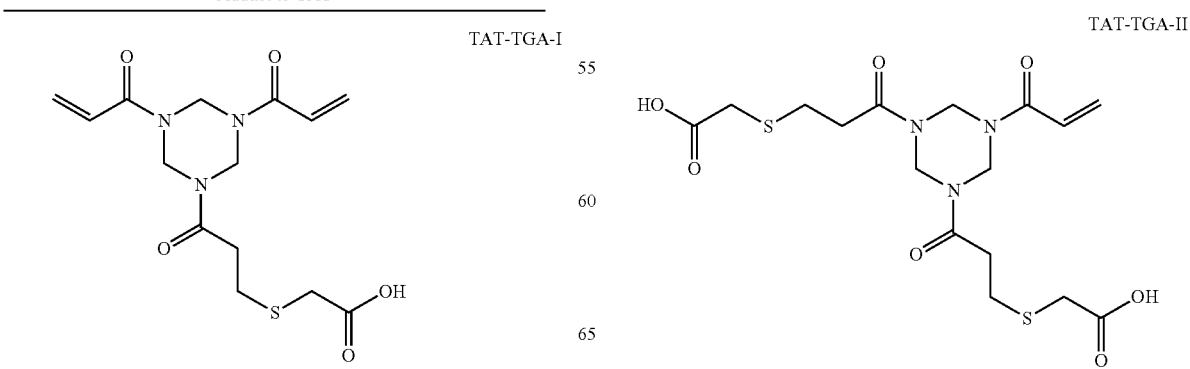

TAT-TGA-III
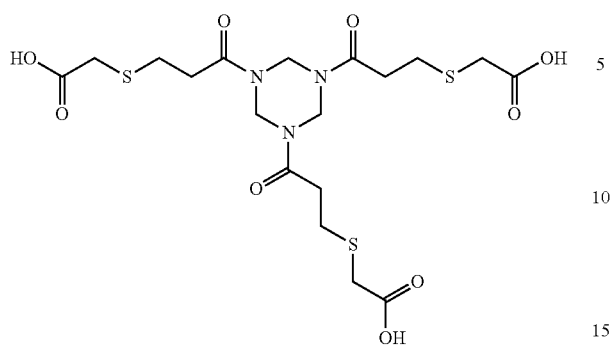
Scheme 15: Reaction to Adhesive Monomer from All-substituted ME Adduct to TAT
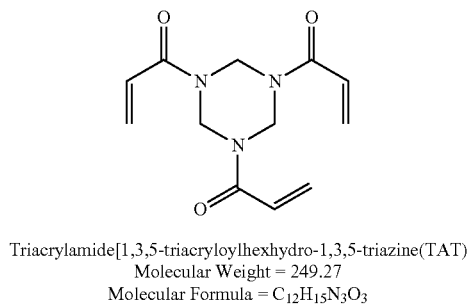
Triacrylamide[1,3,5-triacryloylhexhydro-1,3,5-triazine(TAT)
Molecular Weight = 249.27
Molecular Formula = $C_{12}H_{15}N_3O_3$
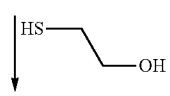
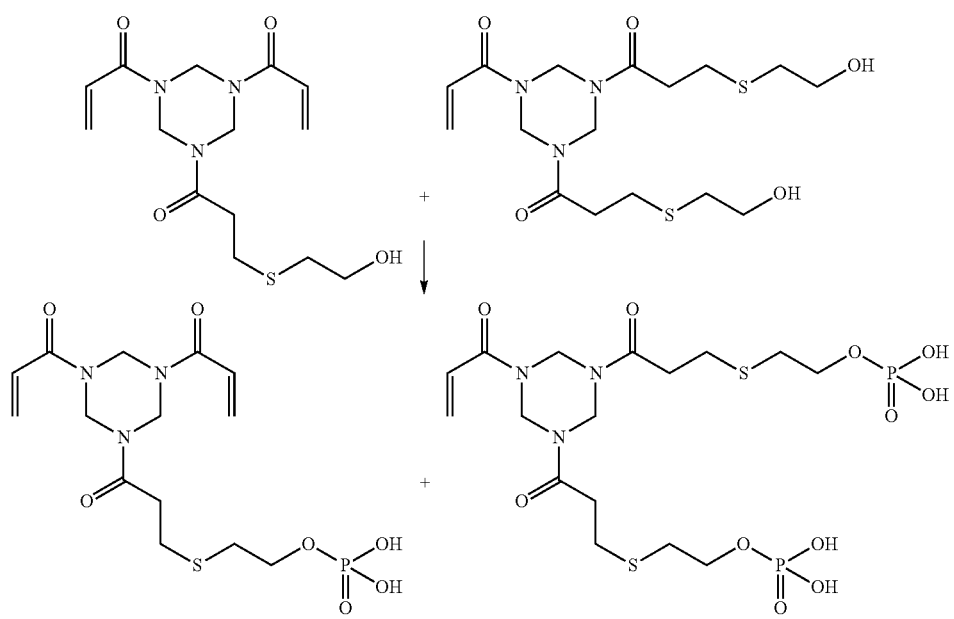

Scheme 16: Reaction to Adhesive Monomer from All-substituted GLT Adduct to TAT

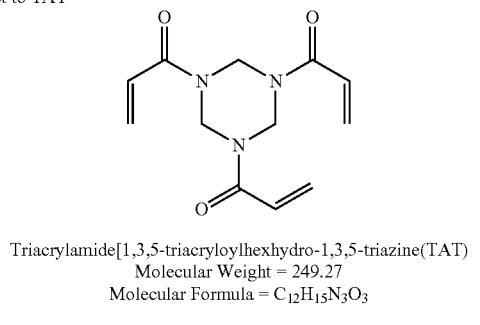

Triacrylamide[1,3,5-triacryloylhexhydro-1,3,5-triazine(TAT)
Molecular Weight = 249.27
Molecular Formula = $C_{12}H_{15}N_3O_3$ TGA
Molecular Weight = 92.12
Molecular Formula = $C_2H_4O_2S$

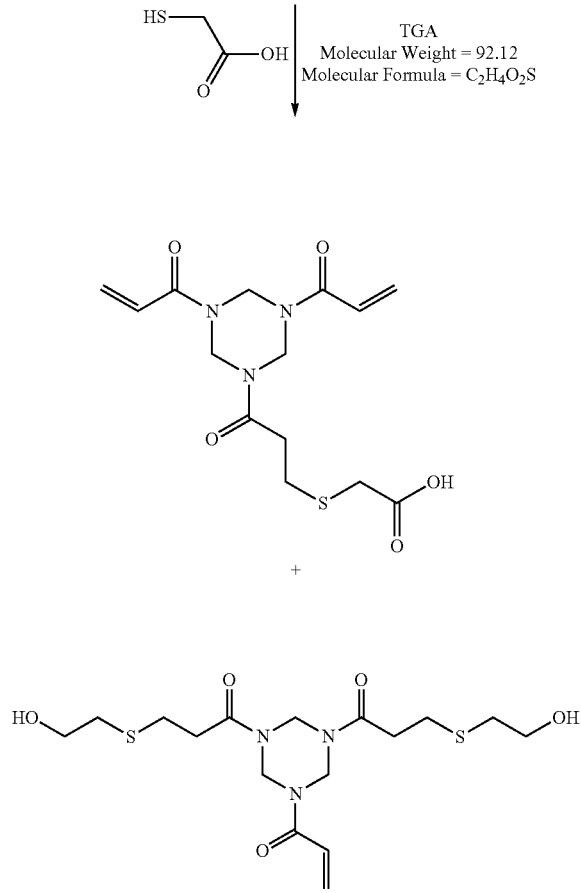

Antibacterial Testing

ISO 22196 method was used for contact to kill testing. Formulated composites of Examples 9-11 and 16-18 containing 1-2% wt/wt of said polymerizable TAT derived resins containing imidazolium moieties were cured in 50 mm×50 mm×2 mm prisms. The test substances were placed in sterile petri dishes. Overnight culture of the test organism, S. aureus ATCC 6538, was diluted in 1:500 Nutrient Broth (NTB) to create the test inoculum. 0.400 ml of the test inoculum was added to each carrier and a sterile 40 mm×40 mm cover film was place over the inoculum to facilitate spreading. Tryptic soy broth (TSB) was used as the growth medium. Carriers were incubated for 24 hrs then harvested with 10 ml of Dey/Engley(D/E) broth. After the 24 hr contact time, there was no visible drying of the inoculum on the carriers. Standard dilution and plating techniques were used for enumeration. Results are shown below in Table IV.

TABLE IV

Antibacterial Test for Cured Composites with Antibacterial Resin

| Test Micro-organism | Time Point | Carrier Type | CPU/Carrier | Percent Reduction Compared to Control after 24 hrs | Log Reduction Compared to Control after 24 hrs |
|---|---|---|---|---|---|
| S. aureus ATCC 6538 | Time Zero | ATL Control | 2.35E+05 | N/A | |
| | | IJ3-136 Control | 1.64E+05 | | |
| | | Ex. 11 | <5.00E+00 | >99.997% | >4.51 |
| | | Ex. 10 | 5.00E+00 | 99.997% | 4.51 |
| | | Ex. 9 | <5.00E+00 | >99.997% | >4.51 |
| | | Ex. 16 | <5.00E+00 | >99.997% | >4.51 |
| | | Ex. 17 | <5.00E+00 | >99.997% | >4.51 |
| | | Ex. 18 | <5.00E+00 | >99.997% | >4.51 |

Refractive Index.

Three examples of TAT-derivatives were prepared via a facile thiol-ene addition reaction consistent with the experimental procedures previously described to produce non-aromatic polymerizable resins with high refractive index via partial thiol addition, samples T1, T2 and T3, which were varied in their amount of thiol addition. The reaction scheme for Sample T2 is shown below as Scheme 17.

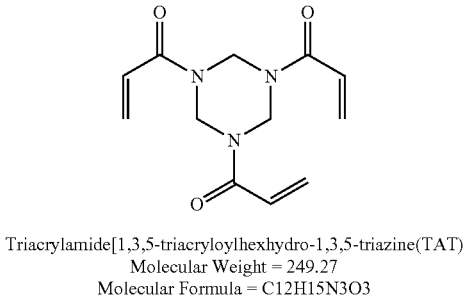

Triacrylamide[1,3,5-triacryloylhexhydro-1,3,5-triazine(TAT)
Molecular Weight = 249.27
Molecular Formula = C12H15N3O3

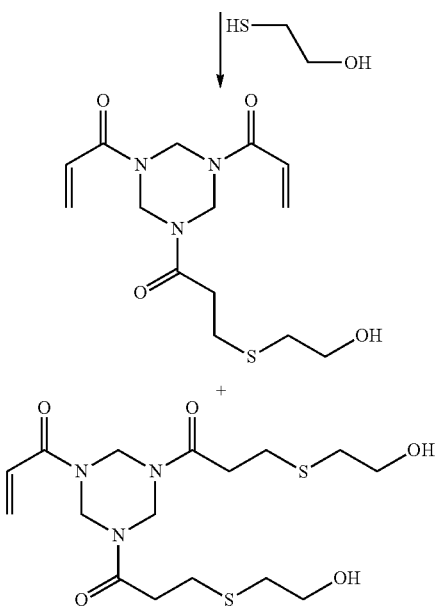

Refractive index of the samples was compared to that of control samples, including numerous aromatic compounds while exhibiting comparable and in some cases higher RI than the control, as shown in Table V.

TABLE V

Refractive Index (RI) for TAT-derivatives and Control Samples

| Resins & Resin Blends | RI @ 25° C. |
|---|---|
| Sample T1 TAT/ME | 1.5592 |
| Sample T2 TAT/ME | 1.5707 |
| Sample T3 TAT/ME/IEM | 1.5348 |
| Control Sample 1 (BisGMA) | 1.5478 |
| Control Sample 2 (UDMA) | 1.4827 |
| Control Sample 3 (TEGDMA) | 1.4580 |
| Control Sample 4 (EBPADMA) | 1.5405 |
| Control Sample 5 (EGAMA) | 1.4505 |

As shown in Table VI, resin blends can be formulated with resins having a lower RI to enhance the overall RI of the blend using up to 20% wt/wt loading in the formulated resins, in which the control sample was an isosorbide resin.

TABLE VI

Effect of Composition of Formulated Resin Blend on Refractive Index (RI)

| Resin Blend | Control Resin % | TEGDMA % | High RI (Sample T2) Resin % | RI @ 20° C. |
|---|---|---|---|---|
| Control Sample 6 | 90 | 10 | 0 | 1.4860 |
| Reformulated Resin 1 | 90 | 3 | 7 | 1.4915 |
| Reformulated Resin 2 | 85 | 4.5 | 10.5 | 1.4925 |
| Reformulated Resin 3 | 80 | 6 | 14 | 1.4930 |
| Reformulated Resin 4 | 75 | 7.5 | 17.5 | 1.4940 |
| Reformulated Resin 5 | 0 | 30 | 70 | 1.5045 |

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A method of forming a hydrolytically-stable and water-soluble polymerizable resin containing a 1,3,5-hexahydro-1,3,5-triazine (TAT) moiety comprising:
    reacting TAT in the presence of a Michael donor to yield mono-substituted TAT resin and di-substituted TAT resin present in a combined amount that is greater than a combined amount of tri-substituted resin TAT and remaining unreacted TAT; and
    adding a (meth)acrylate resin to the mono-substituted TAT resin and di-substituted TAT resin.

2. The method of claim 1, wherein the mono-and di-substituted TAT resins, respectively, have the following general formula:

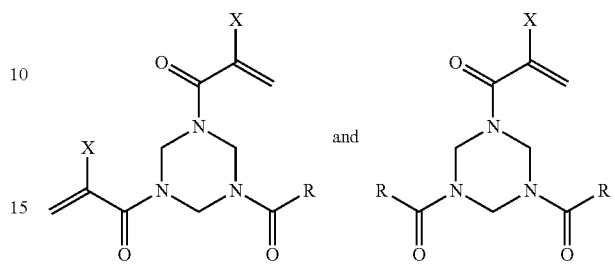

wherein
X is H or CH₃,
R is CH₂CH₂-Y,
Y is —OR', —SR', —NHR", —NR'R", —NR'", or R'—OCO—CH—CO—R'
R' and R" independently or the same are linear or branched linear alkyl having 1 to 18 carbon atoms with or without functional groups, and
R'" is a cyclic alkyl having 2 to 18 carbon atoms or a heterocyclic compound.

3. The method of claim 2, wherein functionalized R' and R" are of the general form R'(R")-Z$_m$, wherein m =1-3 and Z =—OH, —SH, —COOH, COOR'(R")(R'"), —OPO(OH)₂, —OPO(OR')(OH), —PO(OH)₂, —PO(OR')(OH), —OSO₂(OH), aromatics, or substituted aromatics.

4. The method claim 2, wherein —NR'" is imidazole or an imidazole derivative.

5. The method of claim 1, wherein the hydrolysis stable polymerizable resin is reacted in the presence of a compound that yields a resin comprised of a TAT moiety with at least one acrylamide group.

6. The method of claim 1, wherein the hydrolysis stable polymerizable resin is reacted in the presence of a compound that yields a resin comprised of a TAT moiety with at least one inorganic acidic group.

7. The method of claim 1, wherein the hydrolysis stable polymerizable resin is reacted in the presence of a compound that yields a resin comprised of a TAT moiety with at least one imidazolium group.

8. The method of claim 1, wherein the hydrolysis stable polymerizable resin is reacted in the presence of a compound that yields a resin comprised of a TAT moiety with at least one imidazole group.

9. The method of claim 1 further comprising adding a filler material after the step of reacting TAT with the Michael donor.

* * * * *